(12) United States Patent
Adam et al.

(10) Patent No.: US 7,018,430 B2
(45) Date of Patent: Mar. 28, 2006

(54) METHOD OF MASS-COLORING SYNTHETIC MATERIALS

(75) Inventors: Jean-Marie Adam, Rosenau (FR); Jean-Pierre Bacher, Buschwiller (FR)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 18 days.

(21) Appl. No.: 10/484,356

(22) PCT Filed: Jul. 18, 2002

(86) PCT No.: PCT/EP02/07988

§ 371 (c)(1), (2), (4) Date: Jan. 20, 2004

(87) PCT Pub. No.: WO03/010230

PCT Pub. Date: Feb. 6, 2003

(65) Prior Publication Data

US 2004/0194236 A1      Oct. 7, 2004

(30) Foreign Application Priority Data

Jul. 26, 2001   (EP) ................................. 01810735

(51) Int. Cl.
*C08K 5/00*   (2006.01)
*C07D 491/048*   (2006.01)

(52) U.S. Cl. .................... 8/506; 8/637.1; 548/315.7; 548/325.5; 548/326.1; 548/335.1; 548/343.1; 549/456; 549/472

(58) Field of Classification Search .............. 8/506, 8/637.1; 548/315.7, 325.5, 326.1, 335.1, 548/343.1; 549/456, 472
See application file for complete search history.

(56) References Cited

U.S. PATENT DOCUMENTS

| | | | |
|---|---|---|---|
| 3,743,624 A | | 7/1973 | Arnold et al. ............ 260/47 |
| 5,510,403 A | * | 4/1996 | Kaul ...................... 524/90 |
| 5,759,212 A | | 6/1998 | Hall ........................ 8/529 |
| 6,046,335 A | * | 4/2000 | Boeglin et al. ............ 546/32 |

FOREIGN PATENT DOCUMENTS

| | | | |
|---|---|---|---|
| CH | 676241 | | 12/1990 |
| DE | 1121750 | * | 1/1962 |
| DE | 2447228 | * | 3/1974 |
| EP | 0559392 | | 9/1993 |
| EP | 0911332 | | 4/1999 |
| JP | 61-72067 | * | 4/1986 |

OTHER PUBLICATIONS

Abstract of DE 2447228, Jan. 1962.*
T. Tsutsui et al., Polym. Microelectron. Proc. Int. Symp. (1990), pp. 591-600.
Patent Abstracts of Japan Publication No. 07157681 (1995).
Derwent Abstract No. 1997-098670/09 for RU 2061811 (1996).

* cited by examiner

*Primary Examiner*—Margaret Einsmann
(74) *Attorney, Agent, or Firm*—Joseph C. Suhadolnik

(57) ABSTRACT

The present invention relates to a method of mass-coloring synthetic materials, which comprises using at least one pigment dye of formula (1) wherein R and $R_1$ together form a phenyl or heteroaryl radical and $R_2$ is hydrogen, or $R_1$ and $R_2$ together form a phenyl or heteroaryl radical and R is hydrogen, and the rings A and B may each independently of the other be substituted by $C_1$–$C_4$alkyl, $C_1$–$C_4$alkoxy, halogen, —$COOR_3$, —$CONHR_4$ and/or by —$SR_5$, wherein $R_3$, $R_4$ and $R_5$ are each independently of the others hydrogen, $C_1$–$C_4$alkyl, $C_6$–$C_{12}$aryl or heteroaryl, to synthetic materials colored with such pigment dyes, and to novel pigment dyes of formula (3), wherein $R_6$ is hydrogen or bromine

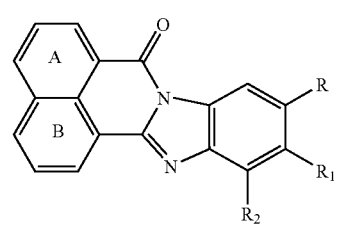

(1)

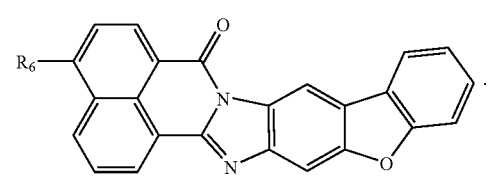

(3)

5 Claims, No Drawings

METHOD OF MASS-COLORING SYNTHETIC MATERIALS

The present invention relates to a method of mass-colouring synthetic materials, as well as to novel pigment dyes based on naphthalimide.

Methods of mass-colouring synthetic materials with pigment dyes are known. It has been shown, however, that the pigment dyes used in that method do not always fully satisfy the highest demands, especially in respect of light fastness, thermostability and/or tinctorial strength, and also do not fully cover the desired range of shades. There is therefore a need for new pigment dyes that yield light-fast, thermostable, tinctorially strong colorations especially in the yellow colour range and that exhibit good allround fastness properties.

It has now been found, surprisingly, that the pigment dyes used in the method according to the invention meet the criteria given above to a considerable degree.

The present invention accordingly relates to a method of mass-colouring synthetic materials, which comprises using at least one pigment dye of formula

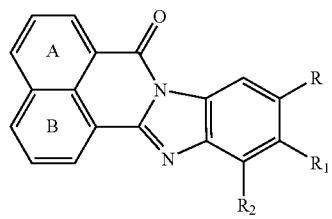

(1)

wherein

R and $R_1$ together form a phenyl or heteroaryl radical and $R_2$ is hydrogen, or $R_1$ and $R_2$ together form a phenyl or heteroaryl radical and R is hydrogen, and the rings A and B may each independently of the other be substituted by $C_1$–$C_4$alkyl, $C_1$–$C_4$-alkoxy, halogen, —$COOR_3$, —$CONHR_4$ and/or by —$SR_5$, wherein $R_3$, $R_4$ and $R_5$ are each independently of the others hydrogen, $C_1$–$C_4$alkyl, $C_6$–$C_{12}$aryl or heteroaryl.

$C_1$–$C_4$Alkyl as a substituent of the rings A and/or B is methyl, ethyl, propyl, isopropyl, n-butyl, isobutyl, sec-butyl or tert-butyl.

$C_1$–$C_4$Alkoxy as a substituent of the rings A and/or B is, for example, methoxy, ethoxy, propoxy or butoxy.

Halogen as a substituent of the rings A and/or B is, for example, fluorine, chlorine or iodine and preferably bromine.

$R_3$, $R_4$ and $R_5$ as $C_1$–$C_4$alkyl are methyl, ethyl, propyl, isopropyl, n-butyl, isobutyl, sec-butyl or tert-butyl.

$R_3$, $R_4$ and $R_5$ as $C_6$–$C_{12}$aryl are, for example, phenyl or naphthyl, which may be unsubstituted or substituted by hydroxy, halogen, $C_1$–$C_4$alkyl and/or by $C_1$–$C_4$alkoxy.

$R_3$, $R_4$ and $R_5$ as heteroaryl are, for example, morpholine, piperidine, thiophene or pyrrole.

The heteroaryl radicals formed by R and $R_1$ or by $R_1$ and $R_2$ are, for example, the radicals of formula

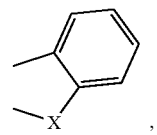

(2)

wherein

X is —O—, —S—, —$NR_6$— and $R_6$ is hydrogen, $C_1$–$C_{12}$alkyl, or phenyl that is unsubstituted or substituted by hydroxy, halogen, $C_1$–$C_4$alkyl and/or by $C_1$–$C_4$alkoxy.

X is preferably —O—.

$R_6$ is preferably hydrogen.

The rings A and B are preferably unsubstituted.

The pigment dyes of formula (1) used in accordance with the invention are known in some cases and can be prepared according to generally known methods.

The pigment dyes of formula

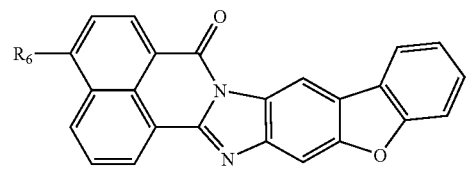

(3)

wherein $R_6$ is hydrogen or bromine, are novel, and the present invention relates also thereto.

The pigment dyes of formula (3) according to the invention are prepared, for example, by reacting a compound of formula

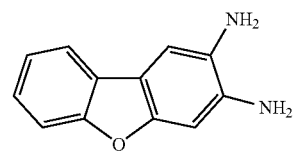

(50)

with an unsubstituted or bromo-substituted naphthalene-1,8-dicarboxylic anhydride and potassium acetate in acetic acid at elevated temperature.

The compounds of formula (50) are known or can be prepared according to known methods.

The present invention relates also to a method for the production of coloured plastics or polymeric colour particles, which comprises mixing together a high molecular weight organic material and a tinctorially effective amount of at least one pigment dye of formula (1).

The colouring of the high molecular weight organic substances with the pigment dye of formula (1) is carried out, for example, by mixing such a pigment dye into those substrates using roll mills, mixing apparatus or grinding apparatus, with the result that the pigment dye is dissolved or finely dispersed in the high molecular weight material. The high molecular weight organic material with the admixed pigment dye is then processed using processes known per se, for example calendering, compression moulding, extrusion, coating, spinning, casting or injection moulding, whereby the coloured material acquires its final form. It is also possible for the admixing of the pigment dye to be carried out immediately prior to the actual processing step, for example by continuously feeding a solid, for example pulverulent, pigment dye and, at the same time, a granulated or pulverulent high molecular weight organic material, and optionally also additional ingredients, e.g. additives, directly into the intake zone of an extruder, where mixing takes place just before processing. In general, however, it is preferable for the pigment dye to be mixed into the high molecular weight organic material beforehand, because more even coloration of the substrates can be obtained.

In order to produce non-rigid mouldings or to reduce their brittleness, it is often desirable to incorporate so-called plasticisers into the high molecular weight compounds prior to shaping. There may be used as plasticisers, for example, esters of phosphoric-acid, phthalic acid or sebacic acid. In the method according to the invention the plasticisers may be incorporated into the polymers before or after the incorporation of the colorant. It is also possible, in order to achieve different shades of colour, to add to the high molecular weight organic materials, in addition to the pigment dye of formula (1), also further pigments or other colorants in any desired amounts, optionally together with further additives, e.g. fillers or siccatives.

Preference is given to the colouring of thermoplastic plastics, especially in the form of fibres. Preferred high molecular weight organic materials to be coloured according to the invention are very generally polymers having a dielectric constant of $\geq 2.5$, especially polyester, polycarbonate (PC), polystyrene (PS), polymethyl methacrylate (PMMA), polyamide, polyethylene, polypropylene, styrene/acrylonitrile (SAN) or acrylonitrile/butadiene/styrene (ABS). Polyester and polyamide are especially preferred. Very special preference is given to linear aromatic polyesters obtainable by polycondensation of terephthalic acid and glycols, especially ethylene glycol, or condensation products of terephthalic acid and 1,4-bis(hydroxymethyl)cyclohexane, for example polyethylene terephthalate (PET) or polybutylene terephthalate (PBTP); also polycarbonates, e.g. those from α,α-dimethyl-4,4-dihydroxy-diphenyl-methane and phosgene, or polymers based on polyvinyl chloride and on polyamides, e.g. polyamide-6 or polyamide-6,6.

The pigment dyes according to the invention impart to the mentioned materials, especially polyester and polyamide materials, tinctorially strong, level yellow colour shades having very good in-use fastness properties, especially good light fastness and good thermostability.

The following Examples serve to illustrate the invention. Unless otherwise indicated, the parts are parts by weight and the percentages are percentages by weight. The temperatures are given in degrees Celsius. The relationship between parts by weight and parts by volume is the same as that between grams and cubic centimeters.

EXAMPLE 1

20.5 parts by weight of 1,2-diaminonaphthalene sulfate together with 14.2 parts by weight of naphthalene-1,8-dicarboxylic anhydride and 23.8 parts by weight of potassium acetate are introduced into 750.0 parts by weight of acetic acid, heated to 100° C. and stirred at that temperature for 15 hours. The reaction mixture is then cooled and diluted with 1000 parts by weight of water. The precipitated product is filtered off with suction, washed with water and dried. 31 parts by weight of the pigment dye of formula

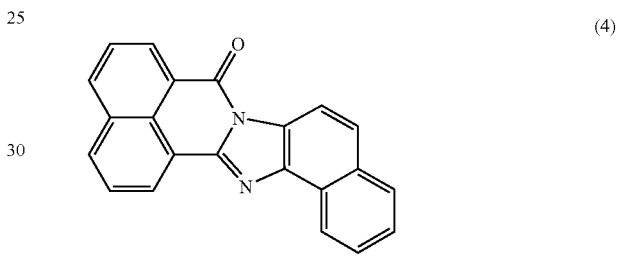

(4)

are obtained. The dye mass-colours polyester and polyamide in light-fast greenish yellow shades having very good thermal stability.

EXAMPLES 2 AND 3

If in Example 1 the 20.5 parts by weight of 1,2-diaminonaphthalene sulfate are replaced by an equivalent amount of a diamino compound indicated in column 2 of Table 1, pigment dyes having the shades indicated in column 4 are likewise obtained.

TABLE 1

| Example | Diamino compound | Pigment dye | Shade in PET |
|---|---|---|---|
| 2 | (2,3-diaminonaphthalene structure with NH₂, NH₂) | (pigment dye structure) | greenish yellow |
| 3 | (diaminodibenzofuran structure with NH₂, NH₂) | (pigment dye structure) | greenish yellow |

EXAMPLES 4–6

If in Examples 1 to 3 the 14.2 parts by weight of naphthalene-1,8-dicarboxylic anhydride are replaced by an equivalent amount of 4-bromo-naphthalene-1,8-dicarboxylic anhydride, the pigment dyes indicated in Table 2 having the shades indicated in column 4 are obtained.

cooled with water, granulated in a granulator (Turb Etuve TE 25 from MAPAG AG, CH-3001 Bern) and then dried for 4 hours at 130° C.

The resulting yellow-coloured polyester granules have good allround fastness properties, especially very good light fastness and high-temperature light fastness properties.

TABLE 2

| Example | Diamino compound | Pigment dye | Shade in PET |
|---|---|---|---|
| 4 | | | yellow |
| 5 | | | yellow |
| 6 | | | greenish yellow |

Dyeing Example 1

1200.00 g of polyester granules (PET Arnite D04-300, DSM) are pre-dried for 4 hours at 130° C. and then mixed homogeneously with 2.4 g of the pigment dye of formula

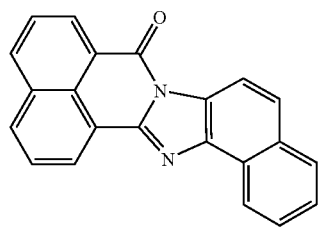

(4)

in a "roller rack" mixing apparatus for 15 minutes at 60 revolutions per minute.

The homogeneous mixture is extruded in an extruder (twin screw 25 mm from Collin, D-85560 Ebersberg) with 6 heating zones at a maximum temperature of 275° C.,

Dyeing Example 2

1200.00 g of polyamide-6 granules (Ultramid B3K, BASF) are pre-dried for 4 hours at 75° C. and then mixed homogeneously with 2.4 g of the pigment dye of formula

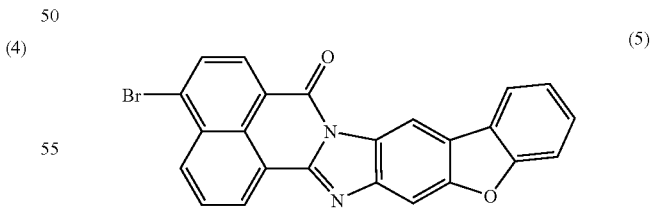

(5)

in a "roller rack" mixing apparatus for 15 minutes at 60 revolutions per minute.

The homogeneous mixture is extruded in an extruder (twin screw 25 mm from Collin, D-85560 Ebersberg) with 6 heating zones at a maximum temperature of 220° C., cooled with water, granulated in a granulator (Turb Etuve TE 25 from MAPAG AG, CH-3001 Bern) and then dried for 4 hours at 75° C.

The resulting yellow-coloured polyamide granules have good allround fastness properties, especially very good light fastness and high-temperature light fastness properties.

What is claimed is:

1. A method of mass-colouring synthetic materials, which comprises incorporating at least one pigment dye of formula

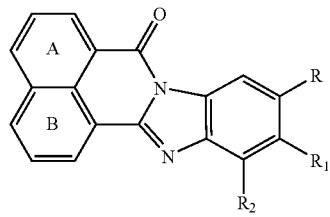

(1)

wherein

R and $R_1$ together form a heteroaryl radical of formula

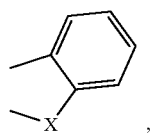

(2)

wherein

X is —O—, —S—, —NR$_6$— and $R_6$ is hydrogen, $C_1$–$C_{12}$alkyl, or phenyl that is unsubstituted or substituted by hydroxy, halogen, $C_1$–$C_4$alkyl and/or by $C_1$–$C_4$alkoxy and $R_2$ is hydrogen, or $R_1$ and $R_2$ together form a phenyl or heteroaryl radical of formula 2 and R is hydrogen, and the rings A and B may each independently of the other be substituted by $C_1$–$C_4$alkyl, $C_1$–$C_4$alkoxy, halogen, —COOR$_3$, —CONHR$_4$ and/or by —SR$_5$, wherein $R_3$, $R_4$ and $R_5$ are each independently of the others hydrogen, $C_1$–$C_4$alkyl, $C_6$–$C_{12}$aryl or heteroaryl.

2. A method according to claim 1, wherein $R_1$ and $R_2$ together form a phenyl radical.

3. A synthetic material coloured according to claim 1.

4. A pigment dye of formula

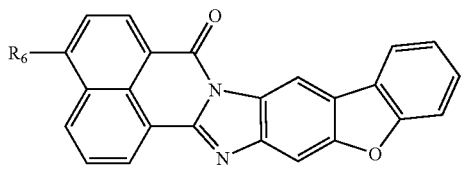

(3)

wherein $R_6$ is hydrogen or bromine.

5. A process for the preparation of a pigment dye of formula (3) according to claim 4, which comprises reacting a compound of formula

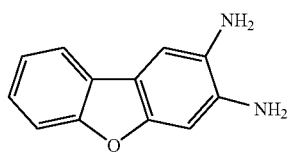

(50)

with an unsubstituted or bromo-substituted naphthalene-1,8-dicarboxylic anhydride and potassium acetate in acetic acid at elevated temperature.

* * * * *